(12) United States Patent
Anderson, Jr. et al.

(10) Patent No.: US 6,468,804 B1
(45) Date of Patent: Oct. 22, 2002

(54) SUPPRESSOR FOR CONTINUOUS ELECTROCHEMICALLY SUPPRESSED ION CHROMATOGRAPHY AND METHOD

(75) Inventors: James M. Anderson, Jr., Arlington Hts; Raaidah Saari-Hordhaus, Mundelein; Bart C. Benedict, Arlington Hts., all of IL (US); Carl Sims, St. Paul; Yuri Gurner, Mendota Hts, both of MN (US); Hung Anthony Pham, Waukegan, IL (US)

(73) Assignee: Alltech Associates, Inc., Deerfield, IL (US)

( * ) Notice: Subject to any disclaimer, the term of this patent is extended or adjusted under 35 U.S.C. 154(b) by 0 days.

(21) Appl. No.: 09/365,496

(22) Filed: Aug. 2, 1999

(51) Int. Cl.$^7$ .................. G01N 25/08; G01N 30/02; G01N 25/18; G01N 15/06; G01N 33/00; G01N 33/48; G01N 27/02; G01N 27/06; G01N 27/12; B01D 19/00; B01D 15/08; B01D 24/00; B01J 49/00

(52) U.S. Cl. .................. 436/161; 436/149; 436/150; 422/68.1; 422/70; 422/82.02; 210/656; 210/670; 210/198.2; 210/295

(58) Field of Search .................. 210/656, 748, 210/188, 198.2, 295; 436/161, 149, 150; 422/68.1, 70, 82.02

(56) References Cited

U.S. PATENT DOCUMENTS

| | | | | |
|---|---|---|---|---|
| 3,926,559 A | * | 12/1975 | Stevens .................. 23/230 R |
| 4,455,233 A | * | 6/1984 | Pohl et al. .................. 210/635 |
| 4,474,664 A | * | 10/1984 | Stevens et al. .................. 210/656 |
| 4,486,312 A | * | 12/1984 | Slingsby et al. .................. 210/656 |
| 4,861,555 A | | 8/1989 | Mowery, Jr. |
| 5,045,204 A | * | 9/1991 | Dasgupta et al. .................. 210/635 |
| 5,248,426 A | * | 9/1993 | Stillian et al. .................. 210/635 |
| 5,352,360 A | | 10/1994 | Stillian et al. |
| 5,518,622 A | * | 5/1996 | Stillian et al. .................. 210/635 |
| 5,569,365 A | * | 10/1996 | Rabin et al. .................. 204/450 |
| 5,597,481 A | * | 1/1997 | Stillian et al. .................. 210/198.2 |
| 5,633,171 A | | 5/1997 | Small et al. |
| 5,759,405 A | | 6/1998 | Anderson, Jr. et al. |
| 5,759,450 A | * | 6/1998 | Anderson, Jr. et al. ..... 210/656 |
| 5,773,615 A | | 6/1998 | Small et al. |
| 5,914,025 A | | 6/1999 | Small |
| 6,027,643 A | * | 2/2000 | Small et al. .................. 210/198.2 |
| 6,036,921 A | * | 3/2000 | Small et al. .................. 422/70 |
| 6,077,434 A | * | 6/2000 | Srinivasan .................. 210/635 |
| 6,093,327 A | * | 7/2000 | Anderson, Jr. et al. ..... 210/660 |
| 6,200,477 B1 | * | 5/2001 | Anderson, Jr. et al. ..... 210/635 |
| 6,225,129 B1 | * | 5/2001 | Liu et al. .................. 436/161 |

FOREIGN PATENT DOCUMENTS

| | | |
|---|---|---|
| JP | 53-116278 | 10/1978 |
| WO | WO 98/30314 | 7/1998 |
| WO | WO 98/40145 | 9/1998 |
| WO | WO 99/11351 | 3/1999 |
| WO | WO 99/44054 | 9/1999 |
| WO | WO 99/56849 | 11/1999 |

* cited by examiner

Primary Examiner—Jill Warden
Assistant Examiner—B R Gordon
(74) Attorney, Agent, or Firm—Brinks Hofer Gilson & Lione

(57) ABSTRACT

Methods and devices for continuous electrochemically suppressed ion chromatography are disclosed. In preferred aspect of the invention, a chloromatography effluent comprising analyte ions and electrolyte is split into a first chromatography effluent flow stream and a second chromatography effluent flow stream. Electrolysis ions selected from the group consisting of hydronium ions and hydroxide ions are generated by the electrolysis of water. Electrolysis ions of the same charge as the electrolyte and the second chromatography effluent stream are flowed through a stationary phase thereby suppressing the electrolyte in the second chromatography effluent flow stream. The analyte ions are subsequently detected in the suppressed second chromatography effluent flow stream.

39 Claims, 8 Drawing Sheets

SUPPRESSOR FOR CONTINUOUS ELECTROCHEMICALLY SUPPRESSED ION CHROMATOGRAPHY AND METHOD

FIELD OF THE INVENTION

The present invention relates to the field of ion chromatography (IC), and. in particular, to a suppressor for continuous electrochemically suppressed ion chromatography and method.

BACKGROUND OF THE INVENTION

Suppressed ion chromatography (SIC) is a commonly practiced method of ion chromatography which generally uses two ion-exchange columns in series followed by a flow through conductivity detector for detecting sample ions. The first column, called the analytical, chromatography or separation column, separates the analyte ions (e.g., the sample ions) in a sample by elution of the analyte ions through the Column. The analyte ions are flowed through the analytical columns via a mobile phase comprising electrolyte. Generally, a dilute acid or base in deionized water is used as the mobile phase. From the analytical column, the separated analyte ions and mobile phase are then flowed to the second column, Which is called the suppressor or stripper. The suppressor serves two primary purposes: (1) it lowers the background conductance of the mobile phase by retaining (e.g., suppressing)) the electrolyte of the mobile phase, and (2) it enhances the conductance of the analyte ions by converting the analyte ions to their relatively more conductive acid (in anion analysis) or base (in cation analysis). The combination of these two functions enhances the signal to noise ratio, and, thus, improves the detection of the analyte ions in the detector. Accordingly, upon exiting the suppressor, the analyte ions and suppressed mobile phase are then flowed to the detector for detection of the analyte ions. A variety of different types of suppressor devices and methods are discussed in U.S. Pat. Nos. 3,897,213; 3,920, 397; 3,925,019; 3,926,559; and U.S. Ser. No. 08/911,847. Applicants hereby incorporate by reference the entire disclosure of these patent applications and patents.

As those skilled in the art will appreciate, both the mobile phase and the sample contain counterions of the analyte ions. A suppressor operates by ion exchange,e of suppressor ions, which are located in the suppressor, with both (1) the mobile phase electrolyte counterions and (2) the sample counterions. In anion analysis, for example, the suppressor ions normally comprise hydronium ions and the mobile phase comprises electrolyte such as sodium hydroxide or mixtures of sodium carbonate and sodium bicarbonate. In cation analysis, the suppressor ions normally comprise hydroxide ions, and the mobile phase may comprise electrolytes such as hydrochloric acid or methanesulfonic acid. The suppressor ions are located on a stationary phase, which may be an ion exchange, membrane or resin. As the mobile phase and sample (which contains both analyte ions and counterions of the analyte ions) are flowed through the stationary phase of the suppressor, the electrolyte counterions in the mobile phase and the sample counterions are retained on the stationary phase by ion exchange with the suppressor ions. When the suppressor ions are either hydronium or hydroxide, ion exchange of the electrolyte counterions with suppressor ions converts the mobile phase to water or carbonic acid, which are relatively non-conductive. On the other hand, the ion exchange of sample counterions with suppressor ions (i.e., hydronium or hydroxide ions) converts the analyte ions to their relatively more conductive acid (in anion analysis) or base (in cation analysis). Thus, the analyte ions, which are now in their relatively more conductive acid or base form, are more sensitive to detection against the less conductive background of the mobile phase.

However, unless the suppressor ions are continuously replenished during, the suppression process, the concentration of suppressor ions on the stationary phase is reduced. Eventually the suppressor will become exhausted and its suppression capacity is either lost completely or significantly reduced. Thus, the suppressor must be either replaced or regenerated. The need to replace or regenerate the suppressor is inconvenient, may require an interruption in sample analysis, or require complex valving or regeneration techniques known in the art. Methods of electrochemically regenerating an at least partially exhausted suppressor are known in the art. See, for example, U.S. Pat. Nos. 5,633,171 and 5,773,615, which are directed to intermittent electrolytic packed bed suppressors. The assignee of this application also discloses, among other things, similar methods of intermittent electrochemically regenerating of a suppressor in U.S. Pat. No. 5,759,405. A method of an intermittent, but "frequent," chemical regeneration of a suppressor is disclosed in U.S. Pat. No. 5,597,734. One problem associated with such "intermittent" methods of electrochemically regenerating a suppressor is that the suppressor being regenerated must be taken "off-line", that is, while being regenerated the suppressor is not used in a sample or analysis run. An example of a known technique for continuously regenerating a suppressor by continuously replenishing, suppressor ions is disclosed in U.S. Pat. No. 5,352,360.

Another problem associated with SIC is that a separate suppressor unit is usually required, and, therefore, the number of components in the system is increased over traditional IC systems. Traditional IC systems usually contain a mobile phase source, a pump, a sample injector, an analytical column and a detector for detecting the sample ions. In SIC, a separate suppressor unit is added to the system. This, in turn, increases the complexity of the system and also increases extra-column volume which may decrease chromatographic resolution and sensitivity. Therefore, it would be advantageous to have a system of ion suppression chromatography which reduced the number of system components in traditional SIC systems.

Another problem associated with prior art SIC systems is that the mobile phase is converted to a weakly ionized form, which renders the mobile phase unsuitable for reuse. Thus, it would be advantageous if a system of SIC were developed in which the mobile phase is converted back to its strongly ionized form after Suppression and, thus, may be reused.

SUMMARY OF THE INVENTION

In its various aspects, the present invention addresses one or more of the foregoing problems associated with SIC.

In one aspect of the invention, a method of continuous electrochemically suppressed ion chromatography is provided. Analyte ions in a mobile phase comprising electrolyte are separated in a chromatography column resuting in a chromatography effluent comprising electrolyte and separated analyte ions. The chromatography effluent is then split into a first chromatography effluent stream and a second chromatography effluent stream. Electrolysis ions selected from the group consisting of hydronium ions and hydroxide ions are generated by the electrolysis of water. The electrolysis ions having the same charge as the electrolyte and the second chromatography effluent stream, which contains electrolyte and analyte ions, are simultaneously flowed through a stationary phase thereby suppressing the electrolyte in the second chromatography effluent stream. In a preferred aspect of the invention, the electrolysis ions force the electrolyte away from the second chromatography effluent stream and into the first chromatography effluent stream thereby effectively suppressing the second chromatography effluent stream. The analyte ions in the suppressed second chromatography effluent stream are then detected.

In another aspect of the invention, a suppressor adapted for use in a method of continuous electrochemically suppressed ion chromatography is provided. The suppressor comprises an inlet, a first outlet, a second outlet and a third outlet. A first stationary phase comprising ion exchange resin is positioned in the path of fluid flow through the suppressor from the inlet to the third outlet. A second stationary phase comprising ion exchange resin is positioned in the path of fluid flow through the suppressor from the inlet to the first outlet. A first regeneration electrode is positioned at the third outlet and a second regeneration electrode is positioned at the second outlet.

In yet another aspect of the invention, the suppressor further comprises sensor electrodes positioned in the second stationary-y phase for detecting the analyte ions in the suppressor.

In yet another aspect of the invention, a method of suppressed ion chromatography is provided wherein the suppressed chromatography effluent is converted back to its strongly ionized state after suppression. Thus, the mobile phase is recycled and may be reused in a subsequent sample run.

In a further aspect of the invention, a method of continuous electrochemically suppressed ion chromatography is provided where analytical column effluent, which contains separated analyte ions and electrolyte, is flowed to a first inlet of a suppressor. The suppressor comprises a stationary phase. The chloromatography effluent is flowed through at least a portion of the stationary phase to suppress the chromatography effluent. The suppressed chromatography effluent is flowed to a detector where the analyte ions are detected. The detector effluent is then flowed back to the suppressor through a second inlet and out a second outlet to waste.

In another aspect of the invention, a suppressor is provided wherein the same suppressor may be used in both anion and cation analysis. The suppressor has a first inlet, a first outlet and a second outlet. A first stationary phase is located in the path of fluid flow through the suppressor from the first inlet to the first outlet. A second stationary phase is located in the path of fluid flow through the suppressor from the first inlet to the second outlet. A pair of regeneration electrodes are further provided wherein the first and second stationary phases are located between the electrodes such that an electrical potential may be applied across the first and second stationary phases. The first and second stationary phases further comprise oppositely-charged ion exchange resin.

DESCRIPTION OF THE DRAWINGS

FIG. 4a is a cross-section view of the suppressor illustrated in FIG. 4 alone line A—A.

DETAILED DESCRIPTION OF THE PREFERRED EMBODIMENTS OF THE INVENTION

Figure 1:
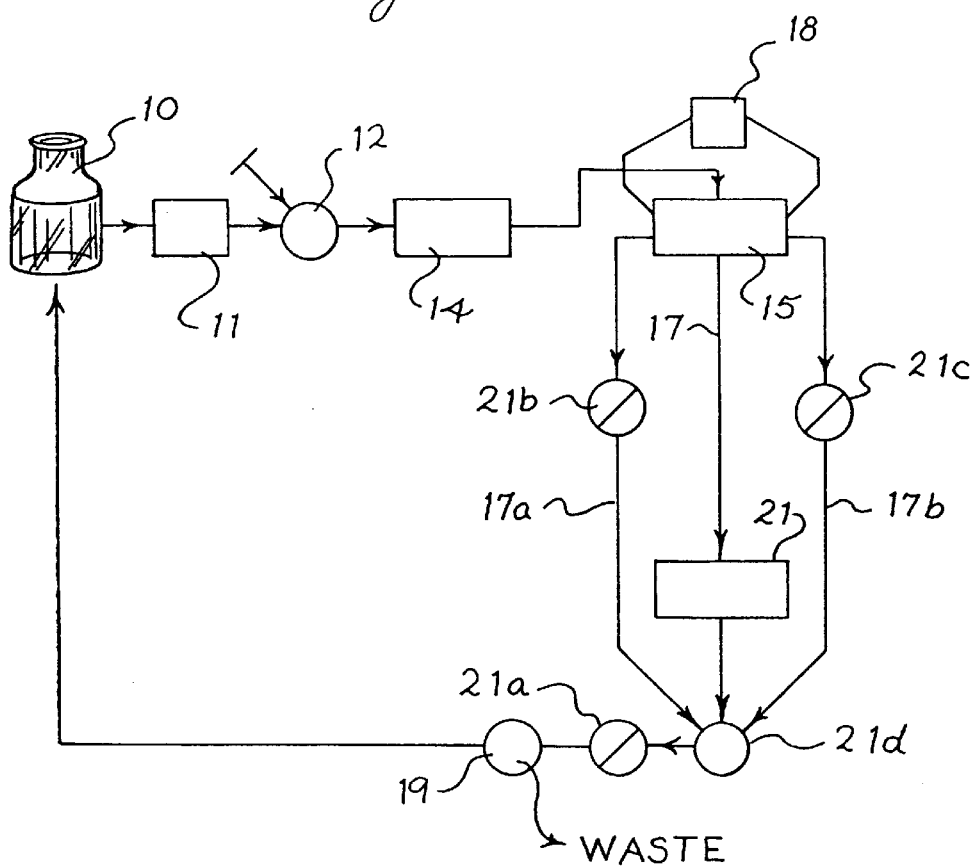
FIGS. 1 and 2 are schematic views of two systems according to the present invention using a suppressor adapted for use in a method of continuous electrochemically suppressed ion chromatography.

FIG. 1 illustrates a system of continuous electrochemically suppressed ion chromatography according to one aspect of the invention. The system comprises a mobile phase source 10 comprising electrolyte, a pump 11, a sample injector 12 and a chromatography column 14, all in fluid communication. The pump 11, sample injector 12 and chromatography column 14 may be selected from the variety of types known by those skilled in the art. For example, preferred pumps include the ALLTECH 526 pump available from ALLTECH ASSOCIATES, INC. (Deerfield, Ill.). Preferred chromatography columns include the ALLTECH ALLSEP or UNIVERSAL CATION COLUMNS. Preferred sample injectors include the RHEODYNE 7725 injection valve.

A suppressor 15 in fluid communication with the chromatography column 14 is further provided. The suppressor 15, which contains electrodes (not shown), is discussed in further detail below. The suppressor 15 is connected to a power source 118. Preferred power sources include the KENWOOD PR36-1.2A. The system also preferably includes a gas permeable tubing or membrane 17 in liquid communication with the suppressor 15 and a detector 21. The ,as permeable tubing is preferably TEFLON AF tubing available from BIOGENERAL of San Diego, Calif. A preferred detector for use in the invention is the ALLTECH MODEL 550 CONDUCTIVITY DETECTOR. Other suitable detectors for use with the present invention are electrochemically detectors. The detector 21 measures or records the analyte ions detected by the detector. Finally, back pressure sources.21a, 21b and 21c are preferably included to control operating pressure in the system. By manipulating the operating pressure, as bubbles from the electrolysis may be controlled.

In operation, the direction of fluid flow is as follows. The mobile phase is flowed from mobile phase source 10 by pump 11 through injection valve 12 to chloromatography column 14 to suppressor 15 and then to detector 21. Upon exiting the detector 21, the mobile phase is flowed through a cross 21d through back pressure regulator 21a and then to recycling valve 19, which directs fluid flow either to waste or back to mobile phase source 10 as discussed below. The recycling valve 19 is preferably a three-way valve.

Figure 2:
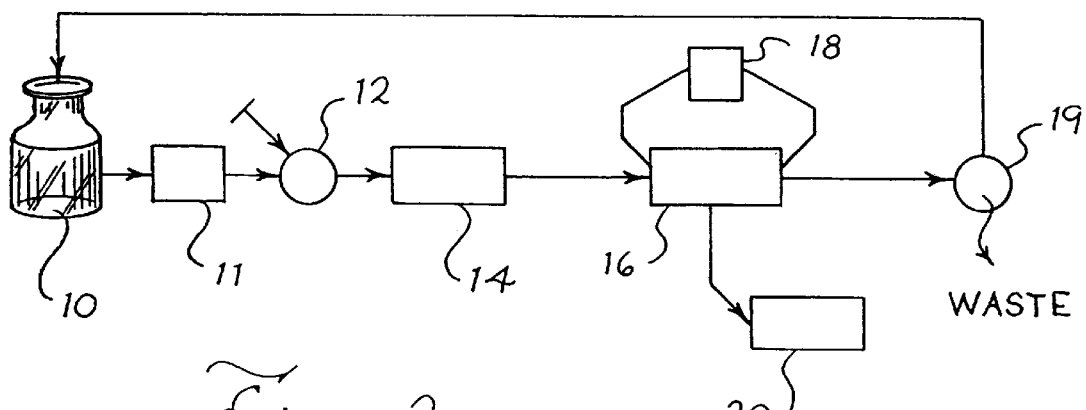

FIG. 2 illustrates another system for use in the method of continuous electrochemically suppressed ion chromatography according to the present invention. This system differs from the system of FIG. 1 in that the suppressor and detector are integrated to give an integrated suppressor and detector 16. The integrated suppressor and detector 16 has sensor electrodes (not shown) for detecting analyte ions and is discussed in further detail below. Additionally, a measuring device 20 is in electrical communication with the integrated suppressor and detector 16 for recording analyte (or sample) ions. A preferred measuring, device is the OAK TON ¼ DIN CONDUCTIVITY AND RESISTIVITY CONTROLLER (OAK TON 100 SERIES). Also in electrical communication with the integrated suppressor and detector 16 is power source 18

The path of fluid flow through the system of FIG. 2 is as follows. Fluid flow is from mobile phase source 10 by pump 11 through injection valve 12 to chromatography column 14 to integrated suppressor and detector 16. Upon exiting the integrated suppressor and detector 16, the mobile phase is flowed through recycling valve 19, which directs fluid flow either to waste or back to mobile phase source 10 as discussed below. The recycling valve 19 is preferably a three-way valve.

According to one aspect of the invention, and with reference to FIG. 1, the mobile phase comprising electrolyte and analyte ions (e.g., sample ions that are to be detected) are flowed to chromatography column 14 where the analyte ions are separated. The separated analyte ions and electrolyte exit the chromatography, Column 14 as chromatography effluent and flowed to suppressor 15 where the electrolyte is suppressed. The operation of suppressor 15 is described with reference to FIG. 3 for anion analysis and a mobile phase consisting of an aqueous solution of sodium hydroxide. As those skilled in the art will quickly appreciate, the invention may easily be adapted for cation analysis and/or different electrolytes.

Figure 3:
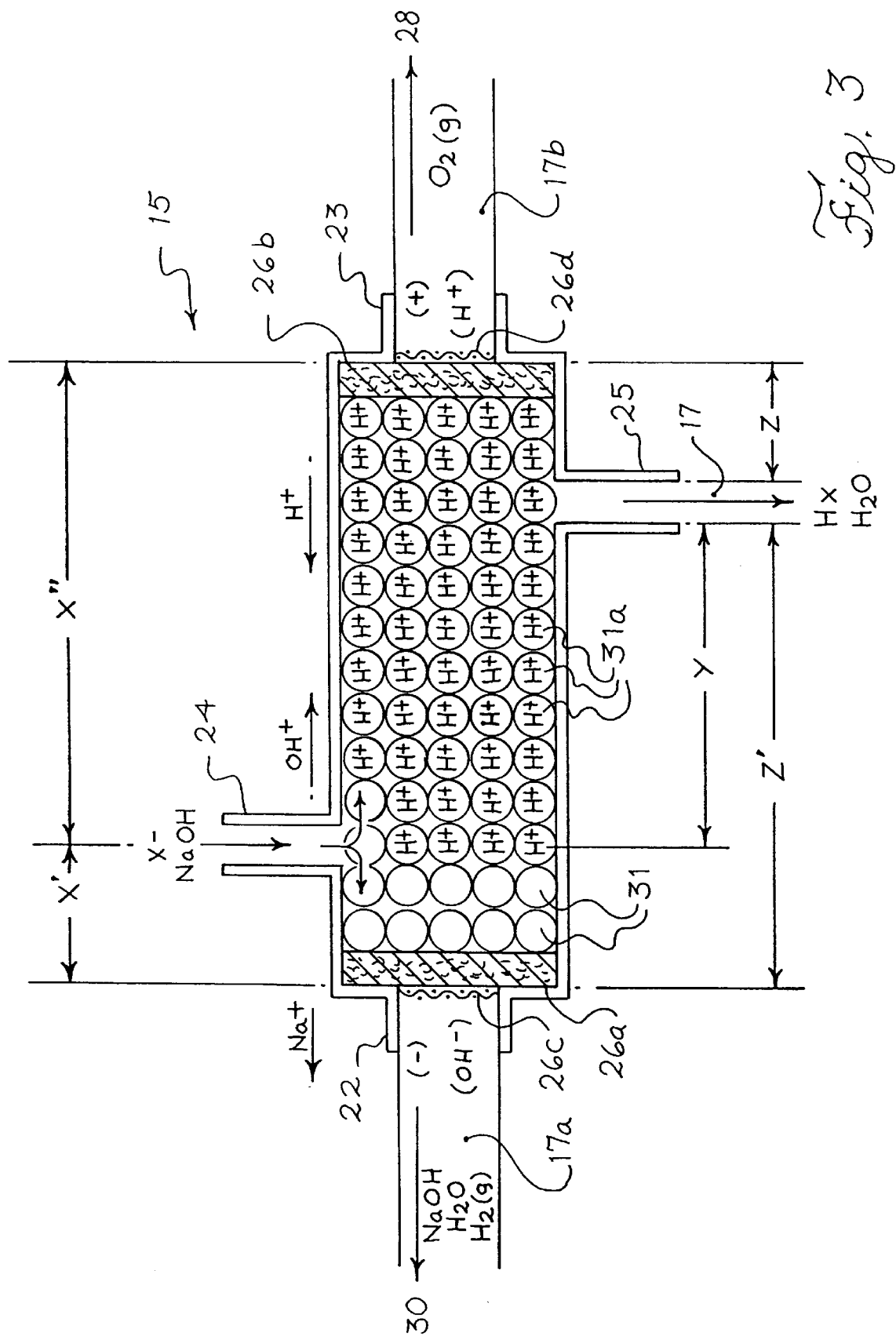
FIG. 3 is a schematic view illustrating the method of operation of a suppressor adapted for use in a method of continuous electrochemically suppressed ion chromatography of the present invention.

Referring to FIG. 3, the suppressor 15 comprises first stationary phase 31 and second stationary phase 31a. By stationary phase, it is meant chromatography packing material comprising ion exchange resin in either free resin form or encapsulated in a membrane matrix that permits liquid flow therethrough. The stationary phase is preferably a strong cation exchanger, such as sulfonic acid cation exchanges such as BIORAD AMINEX 50WX8. The suppressor may also include end filters, 26a and 26b, comprising strong cation exchange resin encapsulated in a TEFLON filter mesh located at both ends of the suppressor 15. These end filters limit the amount of gas, which is generated at the regeneration electrodes during electrolysis, from entering the suppressor 15 during electrolysis. Preferred end filters are ALLTECH NOVO-CLEAN IC-H Membranes. The suppressor 15 further comprises first regeneration electrode 22 and second regeneration electrode 23. In this embodiment, the first regeneration electrode 22 is the cathode and the second regeneration electrode 23 is the anode. The first and second regeneration electrodes are preferably flow-through electrodes that are connected to power source 18 (not shown). The preferred electrodes are made of a titanium housing with flow-through titanium frits, 26c and 26d. The electrodes are platinum plated to provide an inert, electrically-conductive surface. The suppressor 15 further comprises an inlet 24 for receiving the chromatography column effluent and a first outlet 25 for flowing suppressed chromatography effluent (which contains analyte ions) to the detector 21. The suppressor also comprises second and third outlets 28 and 30, respectively, through regeneration electrodes 23 and 22, respectively.

During a sample run power is continuously applied to activate regeneration electrodes 22 and 23 while providing water to the suppressor 15. The water source may be the chromatography effluent or a separate water source may be provided. In any event, electrolysis of the water Occurs at the regeneration electrodes generating electrolysis ions selected from the group consisting of hydronium ions and hydroxide ions. In the present embodiment, hydronium ions are generated at the anode (second regeneration electrode 23) and hydroxide ions are generated at the cathode (first regeneration electrode 22). The hydronium ions are flowed from the second regeneration electrode 23 across second stationary phase 31a and first stationary phase 31 to first regeneration electrode 22. The hydronium ions eventually combine with the hydroxide ions generated at first regeneration electrode 22 to form water, which may exit the suppressor at third outlet 30.

In operation, the chromatography effluent is introduced into the suppressor 15 at inlet 24. In this embodiment, the chromatography effluent comprises separated anions in an aqueous sodium hydroxide eluant. Upon entering the suppressor at inlet 24, the chromatography effluent is split into two chromatography effluent flow streams; namely a first chromatography effluent flow stream and a second chromatography effluent flow stream. The first chromatography effluent flow stream flows in a first chromatography effluent flow path from the inlet 24 through the first stationary phase 31 positioned between the inlet 24 and the first regeneration electrode 22. Thus, the first chromatography effluent flow path is defined by the flow of the first chromatography effluent flow stream from inlet 24 to first regeneration electrode 22. The first chromatography effluent flow stream may exit the suppressor 15 through the first regeneration electrode 22 and third outlet 30. The second chromatography effluent flow stream flows in a second chromatography effluent flow path from the inlet 24 through second stationary phase 31a, which is positioned between the inlet 24 and the second regeneration electrode 23, to the second regeneration electrode 23. Preferably, a portion of the second chromatography effluent exits the suppressor 15 at first outlet 25 and another portion at second outlet 28 through second electrode 23. The second chromatography effluent stream exiting at first outlet 25 is flowed to the detector where the analyte ions are detected.

In the suppressor, the sodium ion electrolyte in the chromatography effluent preferably migrates from the second chromatography effluent flow stream into the first chromatography effluent flow stream by the combined action of the hydronium ion flow from the second regeneration electrode 23 to the first regeneration electrode 22 and the negative charge at the first regeneration electrode 22. The second chromatography effluent flow stream thus comprises separated anions which combine with the hydronium electrolysis ions to create the highly conductive acids of the analyte anions. The second chromatography effluent flow stream further comprises water that is generated, at least in part, by the hydroxide ions from the sodium hydroxide eluant combining with the hydronium electrolysis ions.

A portion of the second chromatography effluent flow stream exits the suppressor at second and first outlets 28 and 25, respectively. The suppressed second chromatography effluent comprises an aqueous solution of the separated analyte anions in their acid form along with oxygen (as generated at the second regeneration electrode from the hydrolysis of water. Because the oxygen gas may interfere to some extent with the detection of the analyte anions at the detector, the suppressed second chromatography effluent exiting first outlet 25 is preferably flowed through a gas permeable membrane such as gas permeable tubing 17 where the oxygen gas is removed prior to detecting the analyte ions. In this respect, a back pressure source 21a (see FIG. 1) may also be included in the system to create sufficient back pressure to efficiently force oxygen as through gas permeable tubing 17 and out of first suppressor effluent. Similarly, back pressure sources 21b and 21c are likewise provided (see FIG. 1) to provide further pressure control in the system. As can be ascertained from FIG. 3, increasing the backpressure in the suppressed second chromatography effluent stream exiting at outlet 25 could disturb fluid flow through the suppressor 15. Therefore, it is preferable to apply counterbalancing pressure in the second chromatography effluent stream exiting at second outlet 28 and first chromatography effluent stream exiting at third outlet 30. The suppressed second chromatography effluent flow stream exiting suppressor 15 at first outlet 25 is then flowed through the gas permeable tubing 17 to the detector 21 where the analyte ions are detected.

Because power is applied while analyte ions are flowed through the suppressor 15, that is, the regeneration electrodes are continuously activated and an electrical potential is continuously applied across the first stationary phase 31 and second stationary phase 31a, there is a continuous flow of hydronium ions from the second regeneration electrode 23 to the first regeneration electrode 22. It is believed that this continuous flow of hydronium ions allows the second stationary phase 31a in the second chromatography effluent flow path to continuously remain in its substantially unexhausted form. Thus, in the present embodiment, a hydronium form ion exchange resin will remain substantially in its unexhausted or hydronium form in the second chromatography effluent flow stream because sodium ions are substantially precluded from entering the second chromatography effluent flow stream (and thus they are unavailable to exhaust the second stationary phase 31a) and are driven into the first chromatography effluent flow stream. Additionally, although the first stationary phase 31 in the first chromatography effluent flow path may become at least partially exhausted by ion exchange of the sodium ions with hydronium ions, a continuous supply of hydronium ions is available to continuously regenerate the first stationary phase 31 by ion exchange with retained sodium ions.

The first chromatography effluent flow stream will exit the suppressor 15 at third outlet 30 as a third suppressor effluent and will comprise hydroxides of the sample countercations and an aqueous sodium hydroxide solution which is formed from the hydroxide ions generated at the first regeneration electrode 22 combining with, respectively, the sodium ion electrolyte and the hydronium electrolysis ions generated at the second regeneration electrode 23. The third suppressor effluent flow stream further comprises hydrogen gas generated by the electrolysis of water at the first regeneration electrode 22. The third suppressor effluent, in this embodiment, also may contain a portion of the analyte anions. By removing the hydrogen gas through known methods in the art (as, for example, by gas permeable tubing) and removing the analyte anions by known methods, the aqueous sodium hydroxide solution may be reused by flowing it back to the eluant source 10 and using it as the mobile phase in a subsequent sample run. Alternatively, the third suppressor effluent flow stream exiting the suppressor at exit 30 may be flowed to waste.

As those skilled in the art will recognize, the suppressor discussed above may be used in methods for continuous electrochemically suppressed ion chromatography for both anion and cation analysis. Moreover, various eluant may be used such as hydrochloric acid or methanesulfonic acid for cation analysis and sodium carbonate/bicarbonate, sodium hydroxide, or sodium phenolate for anion analysis. The first stationary phase 31 and the second stationary phase 31a may be different or the same. Moreover, within either the first or second chromatography effluent flow paths, the stationary phase may be the same or a combination of free ion exchange resin or ion exchange resin encapsulated in a membrane matrix. The stationary phase, however, must permit fluid flow therethrough and the ion flow as discussed above. Examples of suitable stationary phases for anion analysis include DOWEX 50WX8 and JORDIGEL $SO_3$. Examples of suitable stationary phases for cation analysis include AMIMNEX AG-X8 and ZIRCHROM RHINO PHASE SAX.

As illustrated in FIG. 3, inlet 24 is preferably positioned closer to first regeneration electrode 22 than to second regeneration electrode 23 along a horizontal axis. Thus, the distance that the first chromatography effluent streams travels from inlet 24 to first regeneration electrode 22 is preferably shorter than the distance traveled by the second chromatography effluent stream from inlet 24 to second regeneration electrode 23. Most preferably, the horizontal distance X" between the center of inlet 24 and the second regeneration electrode 23 is about 0.930 inches to about 1.205 inches and the horizontal distance X' between the center inlet 24 and the first regeneration electrode 22 is about 0.466 inches to about 0.741 inches. Preferably, the distance Y between the center axis of inlet 24 and first outlet is about 0.232 inches to about 0.464 inches. The distance Z between first outlet and second electrode is about 0.466 inches to about 0.741 inches. The distance Z' between first outlet and first electrode 22 is preferably about 0.930 inches to about 1.025 inches.

Figure 4:
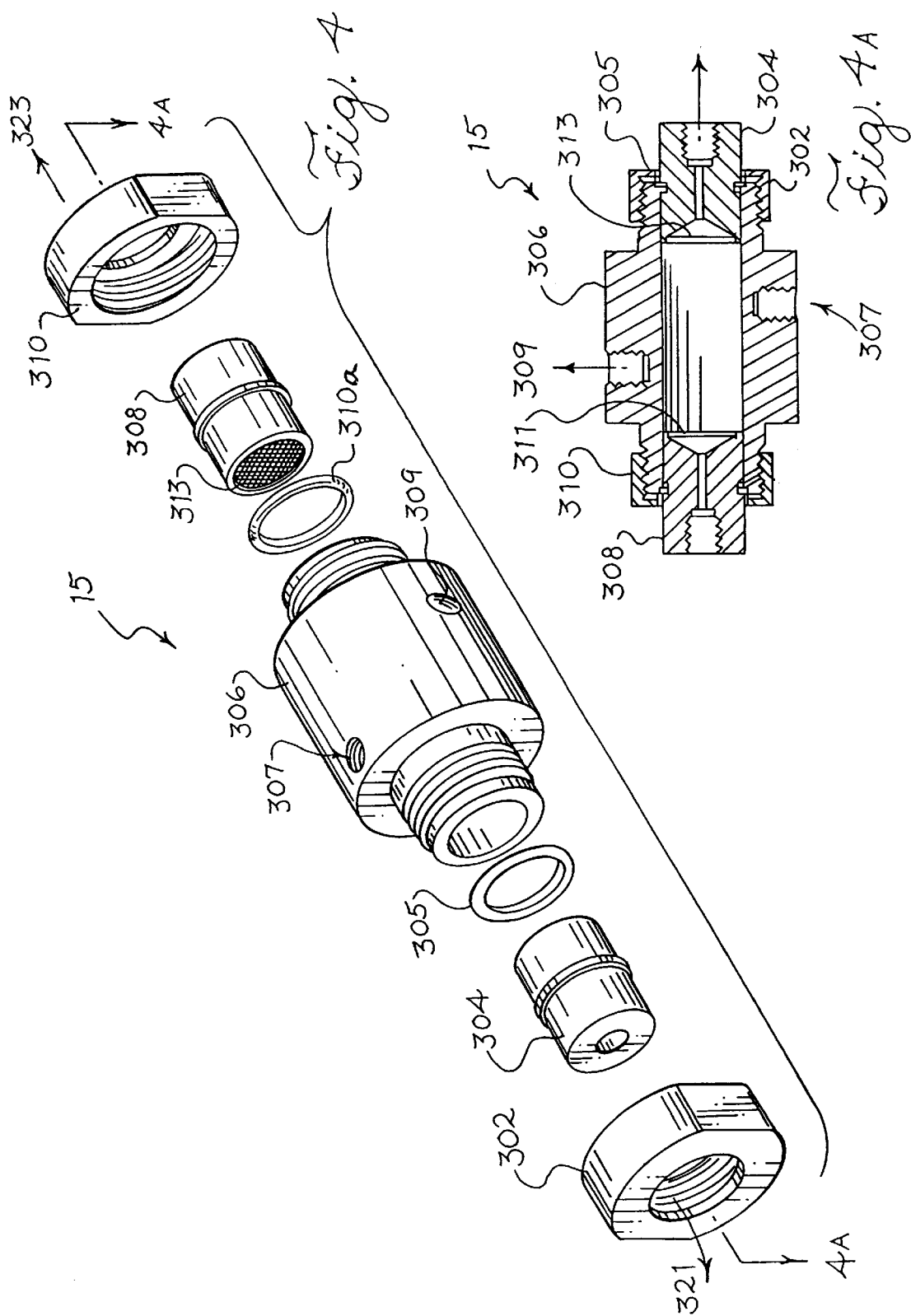
FIG. 4 is an exploded perspective view of a suppressor adapted for use in a method of continuous electrochemically suppressed ion chromatography according to one aspect of the invention.

FIGS. 4 and 4a further illustrate suppressor 15 of the system described with respect to FIG. 1. The suppressor comprises end caps 302 and 310. The suppressor further comprises first regeneration electrode 304 and second regeneration electrode 308. Positioned within first regeneration electrode (not shown in FIG. 4) and second regeneration electrodes are frits 313 and 311, respectively. Frits 313 and 311 are preferably constructed from porous, non-conductive, non-electroactive materials such as polyolefins, or PAT™ (peek alloyed with teflon), or surface-oxidized titanium. Or the frits may preferably be constructed from inert-t, electroactive materials such as platinum coated titanium. The suppressor also includes O-rings 305 and 310a for providing a fluid tight seal between suppressor housing 306 and regeneration electrodes 304 and 308. The suppressor 15 further comprises an inlet 307, a first outlet 309, a second outlet 323 and a third outlet 321.

Preferably, it is desirable to flow the gas bubbles (oxygen and hydrogen gas) formed by the electrolysis away from the detector. Alternatively, it is desirable to remove the gas bubbles from the system prior to the detector. This is desireable because the gas bubbles could interfere with the detection of the analyte ions at the detector. The gas bubbles can be flowed away from, or removed prior to, the detector in a variety of ways. One method for removing gas bubbles prior to the detector was previously illustrated by using gas permeable tubing 17 prior to the detector. By increasing the back pressure in the system using back pressure source 21a, gas bubbles can be "forced" out of the system through gas permeable tubing 17 prior to the detector 21. Of course, it is desireable to balance the back pressure generated by back pressure source 21a, otherwise sample analysis could be affected. Therefore, back pressure Sources 21b and 21c are preferably provided to counter the back pressures generated by Source 21a to permit efficient operation of the system.

Back pressure Sources 21a, 21b and 21c may preferably be constructed front an in-line filter comprising a porous frit of plastic or metal from about 2–10 microns. Instead of two sources 21b and 21c, one such source could be used where the fluid flow in tubing 17a and 17b is merged in a T-configuration into one Such source (not shown). Alternatively, instead of back pressure sources 21b and 21c, the back pressures created by source 21a can be balanced by altering the length of tubing 17a and 17b. Increasing the tubing length increases the back pressure created by the suppressed chromatography effluent flowing therethrough.

In another aspect of the invention, sensor electrodes may be placed in the suppressor 15 resulting in an integrated suppressor and detector. A system for continuous electrochemically suppressed ion chloromatography using an integrated suppressor and detector is illustrated in FIG. 2. In this embodiment, the suppressor described with reference to FIGS. 1, 3, 4, and 4a may be adapted by placing sensor electrodes in the second chromatography effluent flow path. The sensor electrodes are connected to a recording device and the separated analyte ions are detected while in the second chromatography effluent flow path within the suppressor.

Figure 5:
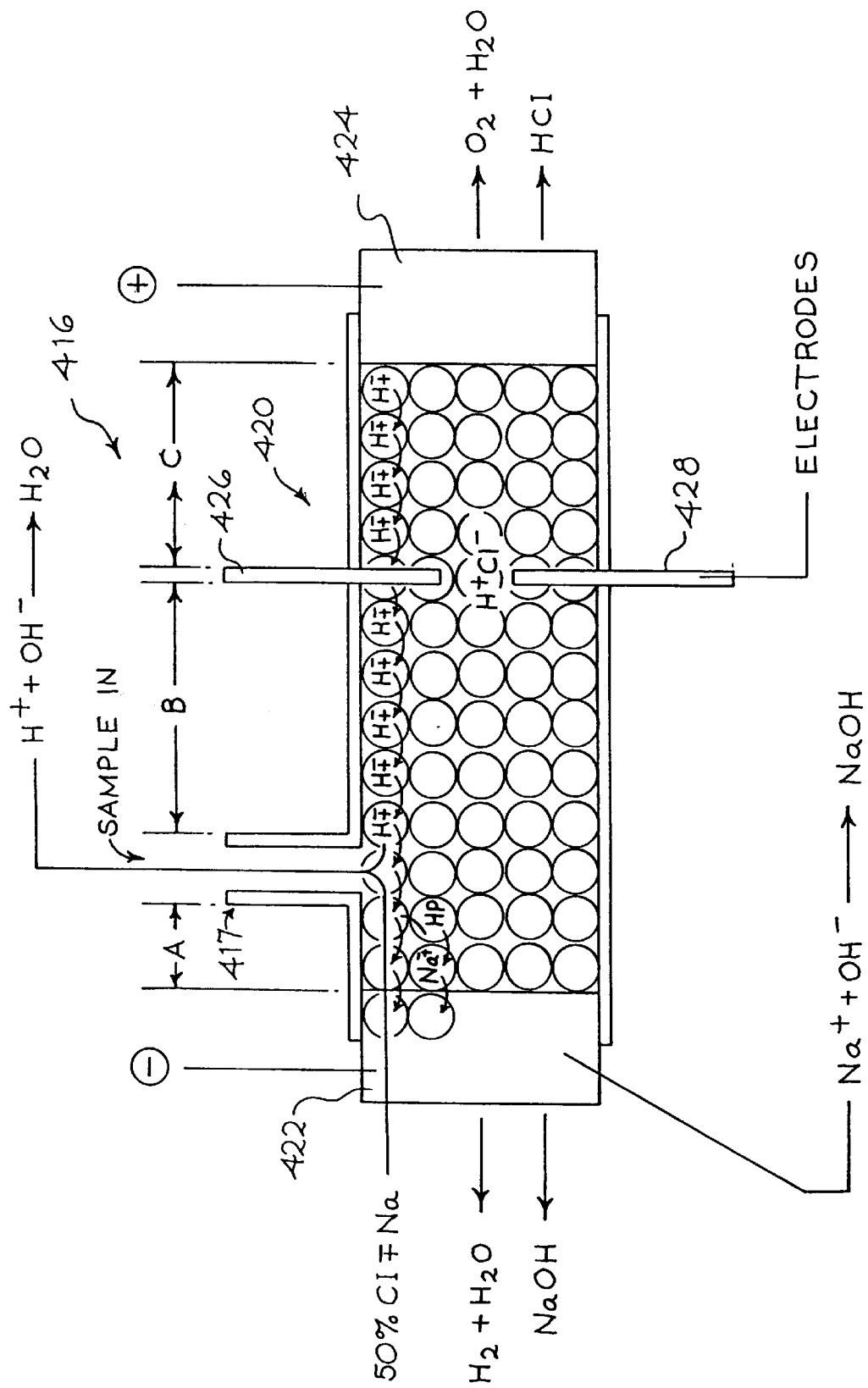
FIG. 5 is an illustration of the method of operation of a suppressor adapted for use in a method of Continuous electrochemically suppressed ion chromatography according to one aspect of the invention wherein the suppressor includes sensor electrodes for detecting analyte ions.

Another adaption of an integrated suppressor and detector is illustrated in FIG. 5. The chromatography effluent is preferably introduced into the integrated suppressor and detector 416 at inlet 417. Upon entering the integrated suppressor and detector, the chromatography effluent is split into two flow paths; namely a First chromatography effluent, flow stream and a second chromatography effluent flow stream much like previously described. The first chromatography effluent flow stream is flowed towards a first regeneration electrode 422 and the second chromatography effluent flow stream is flowed to the second regeneration electrode 424. The first and second regeneration electrodes are preferably flow-through electrodes as previously described. As those skilled in the art will appreciate, by configuring the chromatography effluent flow paths and the regeneration electrodes in this manner, the oxygen and hydrogen gas bubbles formed by the electrolysis of water are flowed away from the sensor electrodes 426 and 428, and, therefore, will not interfere with the detection of the analyte ions at the sensor electrodes 426 and 428.

In ion analysis, the integrated suppressor and detector works as follows. The chromatography effluent comprising aqueous sodium hydroxide and separated analyte anions is flowed from the chromatography column to the integrated suppressor and detector 416. The chromatography effluent is introduced into the suppressor and detector at inlet 417, where the flow path of the chromatography effluent is split. A portion of the chromatography effluent—the first chromatography effluent flow stream—is flowed to the first regeneration electrode 422 and a second portion of the chromatography effluent—the second chromatography effluent flow stream—is flowed to the second regeneration electrode 424. The flow of hydronium ions from the second regeneration electrode 424 to the first regenerations electrode 422 causes the sodium ions and sample countercations to migrate towards the first regeneration electrode 422 (the cathode) and away from the sensor electrodes 426 and 428, which are positioned in the second chromatography effluent flow path.

Additionally, the sodium ions, the sample countercations, and the hydronium ions combine with the hydroxide ions generated at the first regeneration electrode 422 to form an aqueous sodium hydroxide and sample countercation hydroxide solution that may be reused as the mobile phase.

Thus, because sodium ions migrate towards the first regeneration electrode 422 and away from the sensor electrodes 426 and 428, the hydronium ion concentration in the area around the sensor electrodes 426 and 428 far exceeds the sodium ion concentration. The analyte anions combine with hydronium ions to form the relatively more conductive acid of the analyte ion in the areas around the sensor electrodes which increases the sensitivity of the analyte ions to detection in the area around the sensor electrodes. After detection, the acid of the analyte ions is flowed through second regeneration electrode 424 and out of the integrated suppressor and detector 416 . Moreover, the electrolysis of water provides a continuous supply of hydronium ions at regeneration electrode 424 that are flowed across the stationary phase 420 to first regeneration electrode 422. The source of the water for the electrolysis may be from the aqueous chromatography effluent or from a separate aqueous regenerant source.

The previously described embodiments offer certain advantages. For example, gas bubbles formed by the electrolysis of water are flowed away from the sensor electrodes, which reduces the extent to which these bubbles interfere with the detection of the analyte ions. Additionally, the analyte ions do not have to flow through, or be in contact with, regeneration electrodes before detection by the sensor electrodes. This reduces the possibility that analyte ions will be chemically altered by contact with the regeneration electrodes. The concentration of unwanted counter ions of the analyte ions in the area of the sensor electrodes is reduced which increases sensitivity of the system. On this point, it has unexpectedly been discovered that the above-described T-cell embodiment produces greater sensitivity over conventional suppressor systems. Without being restricted to theory; it is presently believed that this increased sensitivity is due to the preferential migration of incoming analyte ions toward the oppositely charged regeneration electrode which concentrates the analyte ions in the area of the sensor electrodes, provided of course the sensor electrodes are positioned near the oppositely charged regeneration electrode as illustrated in FIG. 5.

With further reference to FIG. 5, the horizontal distance A between first regeneration electrode and inlet 417 is preferably about 0.406 inches to about 0.509 inches. The horizontal distance B between inlet 417 and sensor electrodes 426 and 42S is preferably about 0.447 inches to about 0.522 inches. The horizontal distance C between sensor electrodes 426 and 428 and second regeneration electrode 424 is preferably about 0.391 inches to about 0.915 inches.

Figure 6:
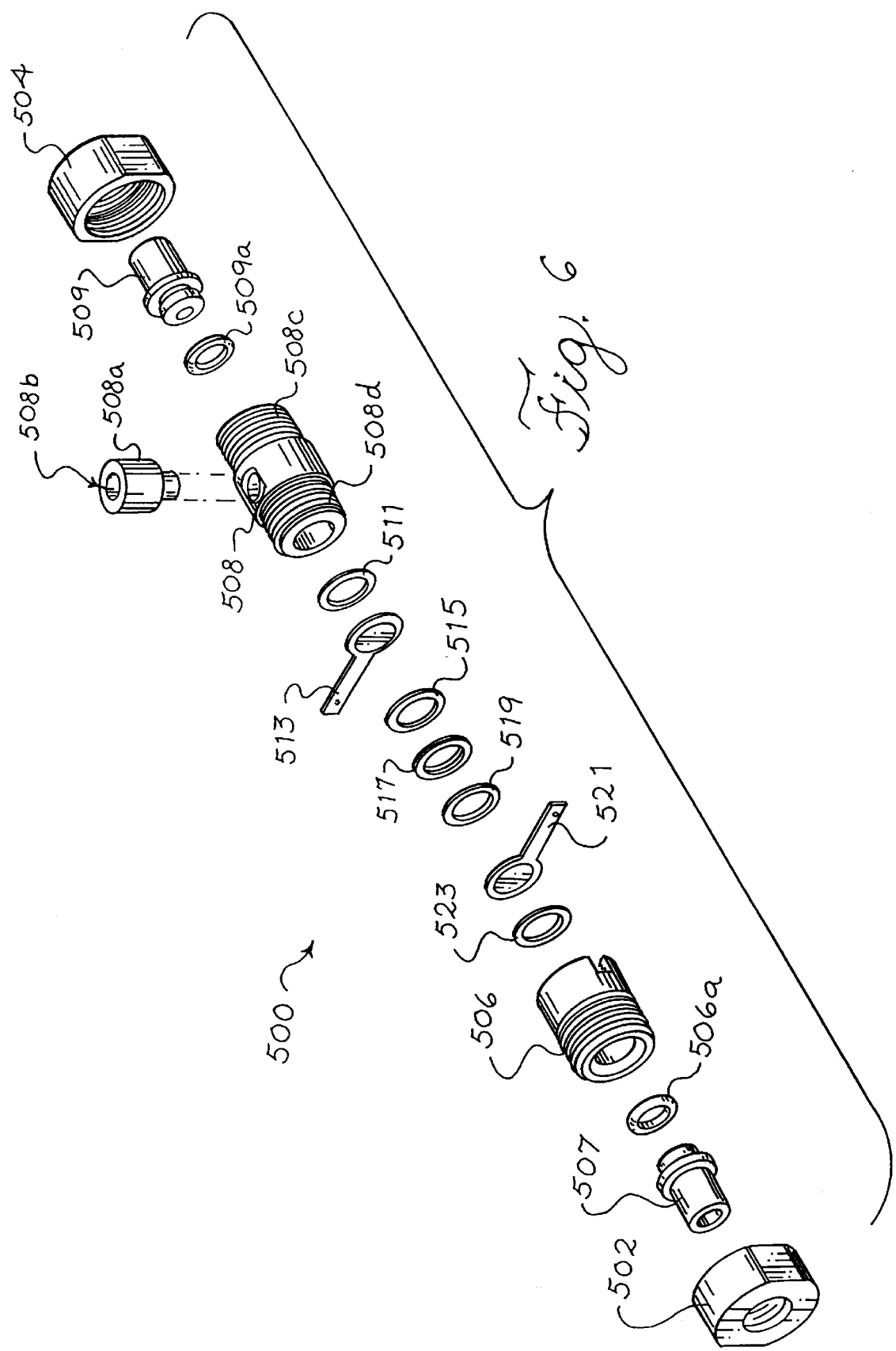
FIG. 6 is an exploded view of an integrated suppressor and detector that may be used according to another aspect of the invention.

FIG. 6 is an exploded view of an integrated suppressor and detector 500 according to one aspect of the invention. First and second end caps 502 and 504 are provided. Positioned within first end cap 502 and a first female cell 506 is first regeneration electrode 507. Positioned within second end cap 504 and a male cell 508 which has threaded ends 508c and 508d, is second regeneration electrode 509. The regeneration electrodes are preferably as described above. Also included are first and second sensor electrodes 521 and 513, respectively. The sensor electrodes are preferably made of inert, conductive materials, such as platinum, gold, or platinum or gold plated stainless steel or titanium. The electrodes must allow liquid flow from the suppressor inlet to regenerate electrode 509, and must therefore either allow flow around or through them. O-rings 506a and 509a are provided to provide a fluid tight seal between first regeneration electrode 507 and female cell 506 and second regeneration electrode 509 and male cell 508, respectively. Spacer 517 and seal gaskets 519 and 515 are positioned between sensor electrodes 513 and 521. The spacer functions to reproducibly set the distance between sensor electrodes 513 and 521 and the gaskets are provided for a fluid tight seal. Seal gaskets 523 and 511 are further provided to give a fluid tight seal between female cell 506 and sensor electrode 521 and male cell 508 and sensor electrode 513, respectively. An adapter 508a is provided for receiving chromatography effluent at inlet 508b. Preferably, end caps 502 and 504, female cell 506, male cell 508 and adaptor 508a are constructed from an electrically non-conductive material, such as PEEK, polyolefin, acrylic, plysulfone, or glass.

Figure 7:
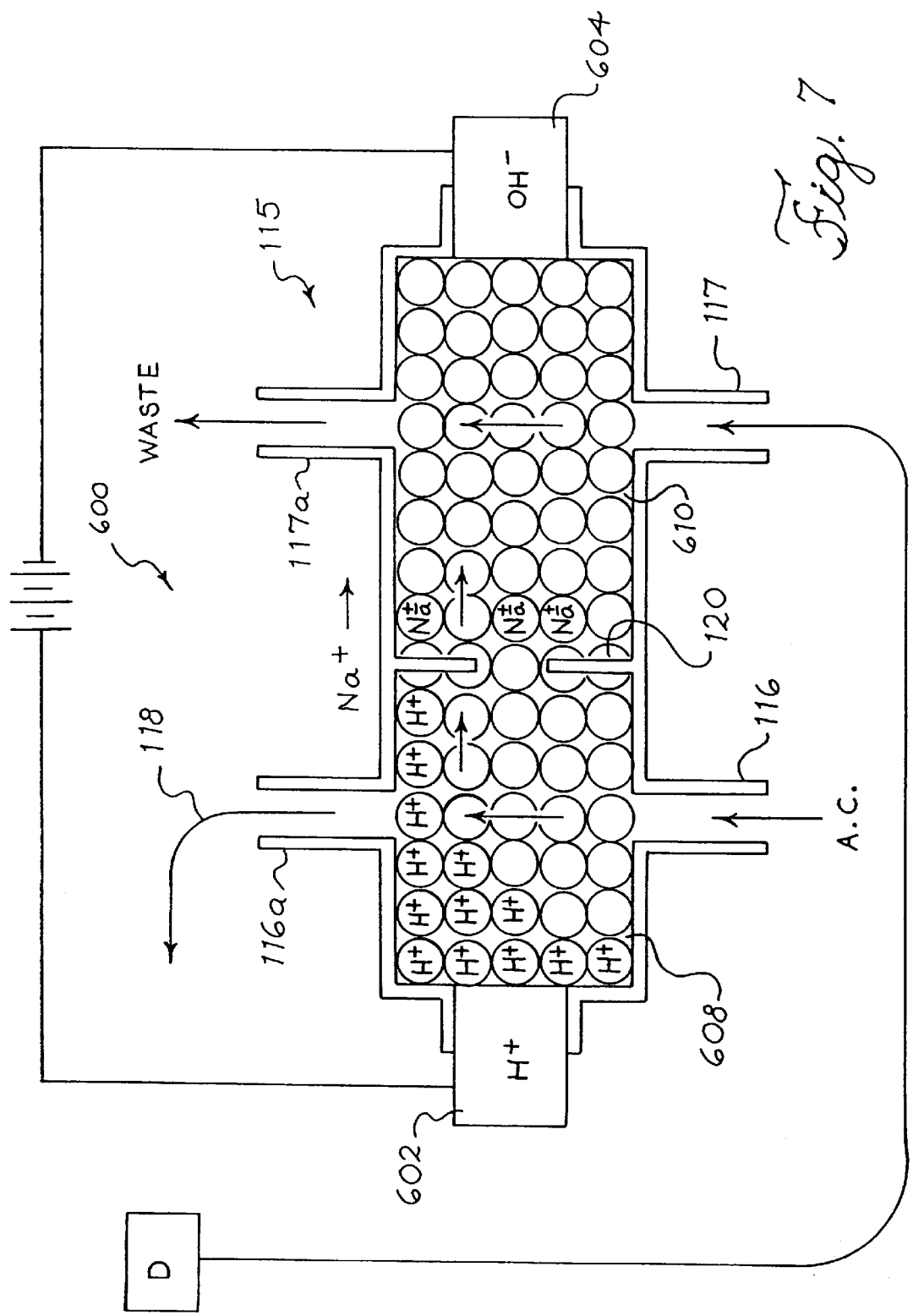
FIG. 7 is an illustration of the operation of a suppressor according to another aspect of the present invention.

FIG. 7 illustrates yet another aspect of the invention using a suppressor without porous electrodes. In this embodiment, the suppressor 600 comprises first and second regeneration electrodes 602 and 604, respectively. The first regeneration electrode 602 is the anode where hydronium ions are generated by the electrolysis of water. Hydroxide ions are generated at the cathode, second regeneration electrode 604. The suppressor further comprises first stationary phase 608 and second stationary phase 610 separated by flow restrictor 120. For anion analysis, the first and second stationary phase is cation exchange packing material as previously described.

The chromatography column effluent is flowed to the suppressor 115 at first inlet 116. Power is applied during the sample run thereby creating an electrical potential across the first and second stationary phase. Using anion analysis in an aqueous sodium hydroxide mobile phase, for example, the chromatography effluent is flowed through the suppressor as indicated by the arrows where suppression occurs as previously described. Sodium ions are driven from the chromatography effluent by the combined action of the hydronium ion flow from anode 602 to cathode 604 and by the attraction of the negative charge at cathode 604. The sample anions are converted to their highly conductive acids by combining with the hydronium ions. The suppressed sample ions are then flowed from first outlet 116a through tubing 118 to the detector (D) where the sample ions are detected. The tubing 118 is preferably gas permeable as previously described. Thus, the gas generated from the electrolysis may be removed prior to the detector through the gas permeable tubing 118 as previously described. The detector effluent may then be flowed back through the suppressor at second inlet 117 and out second outlet 117a and then to waste.

Figure 8:
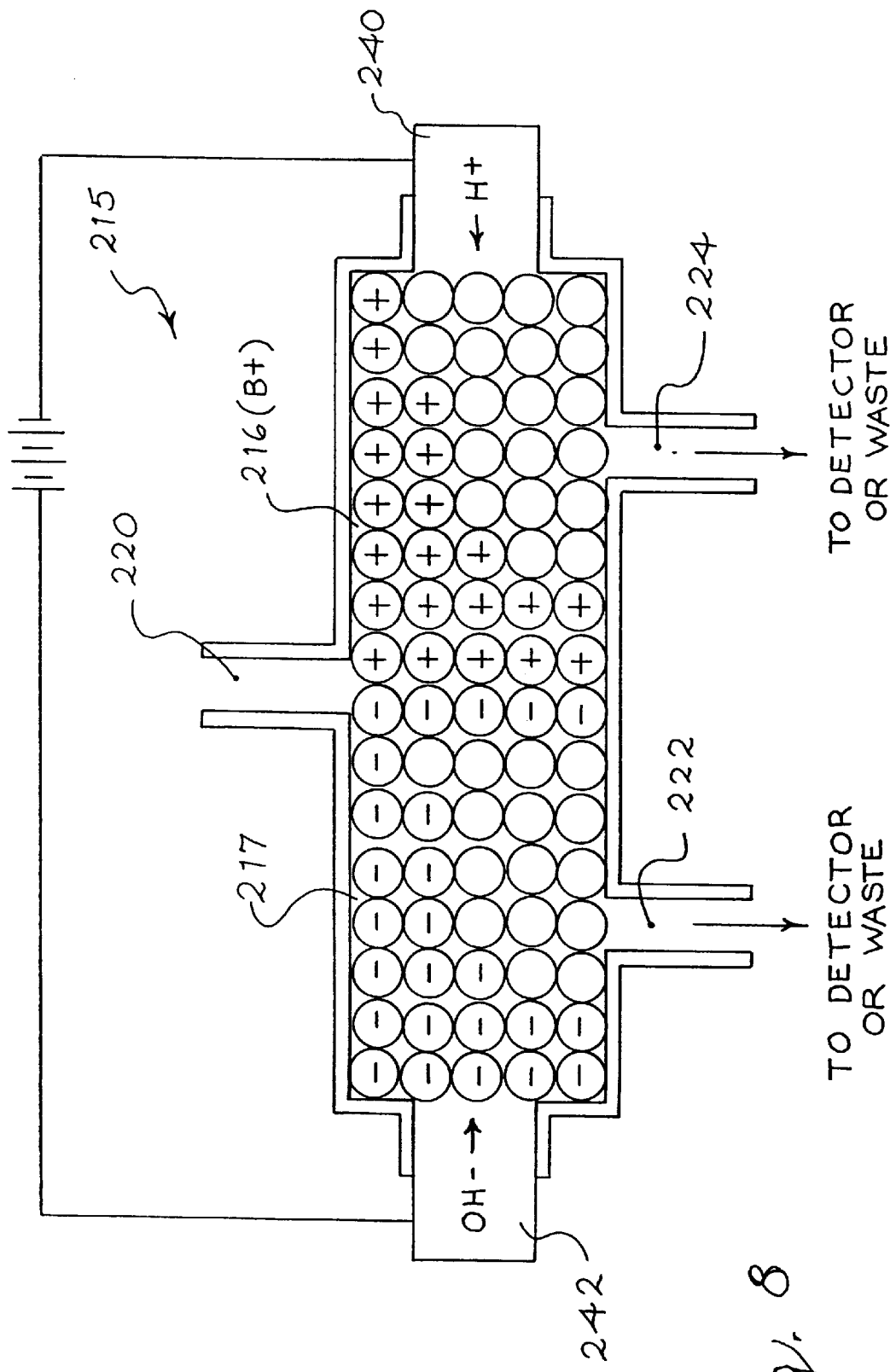
FIG. 8 is an illustration of another suppressor configurational according to the present invention.

FIG. 8 discloses yet another embodiment of the invention where the same suppressor 215 is configured for use in both cation analysis and anion analysis. In this embodiment, the suppressor comprises a first stationary phase 216 comprising cation exchange resin and a second stationary phase 217 comprising anion exchange resin. Preferably, the first and second stationary phase meet at the longitudinal central axis of inlet 220. Chromatography column effluent is flowed from the chromatography column to the suppressor 215 through inlet 220. Depending on whether the sample run comprises anion or cation analyte ions, a detector will be positioned downstream of either first outlet 222 or second outlet 224. Alternatively, detectors may be placed downstream of both outlets 222 and 224. In cation analysis, a portion of the chromatography effluent will flow from the inlet 220 to first outlet 222. Conversely, in anion analysis, a portion of chromatography effluent will flow from inlet 220 to second outlet 224. The same suppressor, therefore, may be used for both cation and anion analysis.

In operation, power is continuously applied thereby creating an electrical potential across the first and second stationary phases during the sample run. Water is supplied to the system, either from the chromatography effluent or from a separate water reservoir, and electrolysis occurs at the first electrode 240 and the second electrode 242. In this embodiment, the first electrode 240 is the anode and the second electrode 242 is the cathode. Hydronium ions are generated at the anode 240 and flowed from the anode towards cathode 242. Hydroxide ions are generated at cathode 242 and are flowed from the cathode towards anode 240.

Thus, in anion analysis, the chromatography effluent is flowed from inlet 220 through first stationary phase 216 where the mobile is suppressed and the sample anions are converted to their conductive acids by ion exchange with hydronium ions. Sodium ions from the mobile phase flow away from first stationary phase 216 and into second stationary phase 217. The sodium ions then exit the suppressor 215 as sodium hydroxide at outlet 222. The suppressed mobile phase and sample anions exit suppressor 215 at outlet 224 and are flowed to the detector where the sample anions are detected. Conversely, the electrolyte of the mobile phase (sodium) migrates to second stationary phase 217 and exits at outlet 222 with the hydroxide ions generated by the electrolysis of water. The stream exiting, at outlet 222 may be treated and re-used as the mobile phase in a subsequent sample run or flowed to waste.

EXAMPLE 1

In this example, a chromatogram was generated using, a Suppressor illustrated in FIG. 3 and the system of FIG. 1 where, instead of back pressure sources 21b and 21c, long length tubing was connected to second and third outlets, 28 and 30, respectively, of the suppressor 15. The following equipment and parameters Were used.

Analytical Column: ALLTECH ALLSEP column (Methacrylate-based anion exchanger with quaternary amine functionalities), 100×4.6 mm; 7 $\mu$m particle size Column Temp: Ambient Eluant: 0.85 mM $NaHCO_3$/0.90 mM $Na_2CO_3$ Flow rate: 10 ml/min.

Detector: Suppressed Conductivity

| Suppressor: (see FIG. 3) | Bed length = 35.5 mm<br>Distance Y = 11.8 mm<br>Distance X" = 23.6 mm | Distance X' = 11.85 mm<br>Distance Z = 11.85 mm<br>Distance Z' = 23.6 mm |
|---|---|---|

Electrodes: Ti frits, 40 $\mu$ porosity and coated with Pt.

Constant Current: 75 mA with corresponding voltage 18V.

Figure 9:
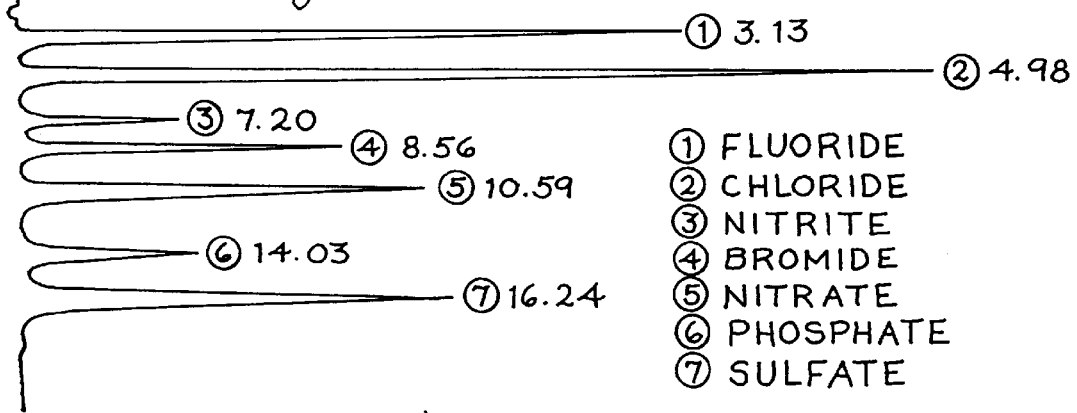
FIG. 9 is a chromatogram generated by the sample run discussed in Example 1.

Tubing exiting at third outlet 30 was 76 inches in length with 0.063" OD and 0.007" ID. Tubing exiting at second outlet 28 was 50 inches in length with 0.063" OD and 0.007" ID. At first outlet 25, and 10 $\mu$ pt frit was provided and tubing to the detector was 0.031" ID and 0.250" OD. The chromatogram of FIG. 9 was obtained.

EXAMPLE 2

Figure 10:
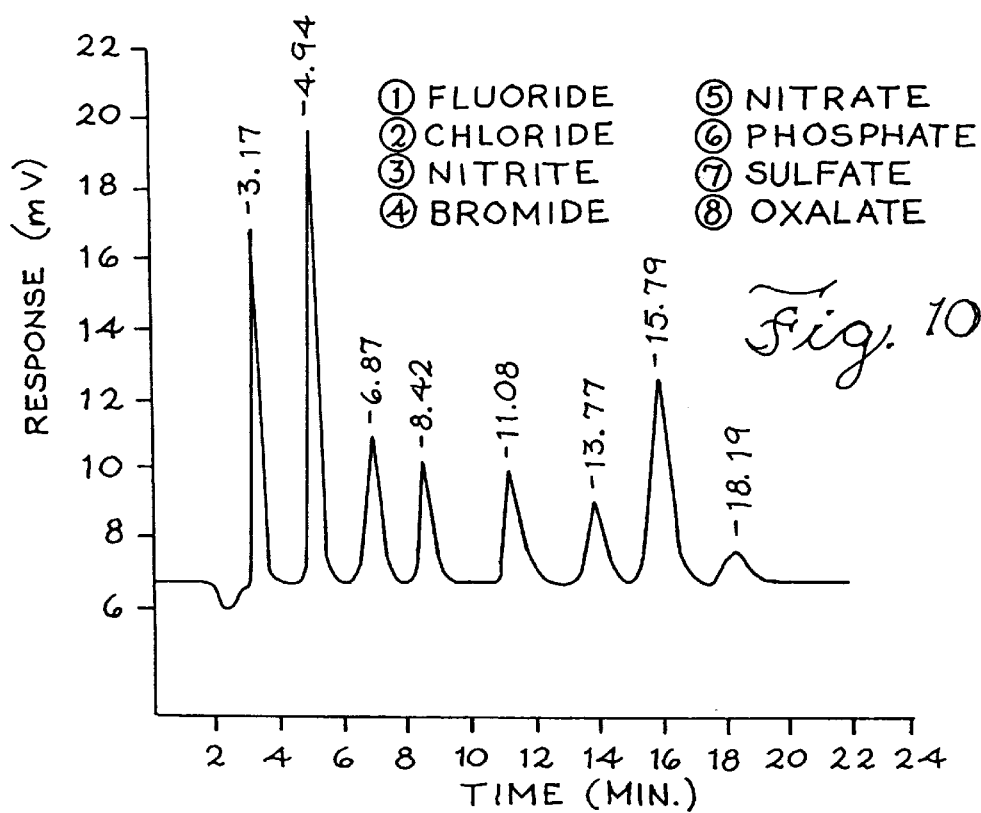
FIG. 10 is a chromatogram generated by the sample run discussed in Example 2.

Similar equipment and parameters as Example 1, except backflow sources (see FIG. 1, reference numerals 21b and 21c were used in the tubing connected to the second outlet 23 and third outlet 30 (see FIG. 3) of the suppressor 15. The backflow sources were placed 5 inches from the anode and cathode. The tubing had 0.040" ID. The backpressure sources were in-line μmicron filters, PEEK alloy TEFLON available from ALLTECH ASSOCIATES, Deerfield, IL. as part no. 68250. An additional 20 inches of tubing was placed on the downstream side of the back pressure sources. Also, in this example, a constant current of 100 mA was applied creating a corresponding voltage of 24V. The chromatogram of FIG. 10 was obtained.

We claim:

1. A method of detecting analyte ions by continuous electrochemically suppressed ion chromatography comprising:
    (a) chromatographically separating analyte ions in an aqueous mobile phase comprising electrolyte to form an aqueous chromatography effluent comprising separated analyte ions and electrolyte;
    (b) flowing the aqueous chromatography effluent through a suppressor comprising an inlet and at least a first and second outlet, a first stationary phase positioned between the inlet and the first outlet, the first stationary phase in electrical communication with a first regeneration electrode, and a second stationary phase positioned between the inlet and the second outlet, the second stationary phase in electrical communication with a second regeneration electrode, wherein a portion of the chromatography effluent flows through the first stationary phase as a first chromatography effluent flow stream and a portion of the chromatography effluent flows through the second stationary phase as a second chromatography effluent flow stream;
    (c) electrochemically driving electrolyte into the first chromatography effluent flow stream and away from the second chromatography effluent flow stream during step (b) by applying an electrical potential across the first and second stationary phase(s), the application of the electrical potential being such that electrolysis ions of opposite charge as the analyte ions are generated at the second regeneration electrode and are flowed from the second regeneration electrode across the second stationary phase towards the first regeneration electrode and thereby driving electrolyte flow into the first chromatography effluent flow stream, which exits the suppressor at the first outlet;
    (d) combining the analyte ions present in the second chromatography effluent flow stream with the electrolysis ions; and
    (e) detecting the analyte ions after step (d).

2. The method of claim 1 wherein the analyte ions comprise anions, the first regeneration electrode is the cathode, the second regeneration electrode is the anode, the electrolyte comprises cations, the electrolysis ions generated at the second regeneration electrode comprise hydronium ions and the analyte ions combine with hydronium ions in step (d) to form an acid of the analyte ions.

3. The method of claim 2 wherein the electrolyte comprises sodium ions.

4. The method of claim 1 wherein the analyte ions comprise cations, the first regeneration electrode is the anode, the second regeneration electrode is the cathode, the electrolyte comprises anions, the electrolysis ions generated at the second regeneration electrode comprise hydroxide ions and the analyte ions combine with hydroxide ions in step (d) to form a base of the analyte ions.

5. The method of claim 1 wherein the second stationary phase remains substantially in its unexhausted form.

6. The method of claim 1 wherein step (e) is performed while the analyte ions are located in the suppressor.

7. The method of claim 1 wherein the first chromatography effluent flow stream exiting the suppressor is reused as a mobile phase in a subsequent analysis run.

8. The method of claim 2 wherein oxygen gas is generated at the anode during the application of the electrical potential in step (b) and is removed from the second chromatography effluent flow stream prior to detecting the analyte ions.

9. The method of claim 4 wherein hydrogen gas is generated at the cathode during the application of the electrical potential in step (b) and is removed from the second chromatography effluent flow stream prior to detecting the analyte ions.

10. The method of claim 1 wherein the first stationary phase and the second stationary phase are selected from the group consisting of free ion exchange resin, ion exchange resin encapsulated in a membrane and mixtures thereof.

11. The method of claim 1 wherein the first and second regeneration electrodes are flow-through electrodes and the first chromatography effluent flow stream exits the suppressor through the first regeneration electrode.

12. The method of claim 1 wherein the first chromatography flow stream exiting the suppressor contains gas selected from the group consisting of oxygen gas and hydrogen gas and the gas is removed prior to using the first chromatography effluent flow stream in a subsequent analysis run.

13. The method of claim 1 wherein electrolyte is substantially precluded from entering the second chromatography effluent flow stream.

14. The method of claim 1 wherein after step (d) but prior to step (e) the second chromatography effluent flow stream is flowed through the second outlet to a detector where the analyte ions are detected.

15. The method of claim 14 wherein electrolytes substantially precluded from entering the detector.

16. The method of claim 1 wherein the electrolyte is substantially precluded from entering the second stationary phase.

17. A method of detecting analyte ions by continuous electrochemically suppressed ion chromatography comprising:
    (a) flowing analyte ions in an aqueous mobile phase comprising electrolyte through an analytical column separating means to form an aqueous chromatography effluent comprising separated analyte ions and electrolyte;
    (b) flowing the aqueous chromatography effluent through a suppressor means for splitting the chromatography effluent into a first chromatography effluent flow stream and a second chromatography effluent flow stream;
    (c) applying an electrical potential in the suppressor means such that electrolyte is electrochemically driven into the first chromatography effluent stream and away from the second chromatography effluent flow stream;
    (d) flowing the second chromatography effluent flow stream out of the suppressor means;
    (e) detecting the analyte ions in the second chromatography effluent flow stream.

18. The method of claim 17 wherein the analyte ions are detected while in the suppressor means.

19. The method of claim 17 wherein the analyte ions are flowed from the suppressor means to a detector after step (c) and prior to step (d).

20. The method of claim 19 wherein the electrolyte is substantially precluded from entering the detector.

21. The method of claim 17 wherein the first chromatography effluent flow stream is reused as a mobile phase in a subsequent sample run.

22. A method of detecting anions by continuous electrochemical suppressed ion chromatography comprising
   (a) chromatographically separating anions in an aqueous mobile phase comprising electrolyte to form an aqueous chromatography effluent comprising separated anions and electrolyte;
   (b) flowing the aqueous chromatography effluent through a suppressor stationary phase that is in electrical communication with an anode and a cathode;
   (c) driving the electrolyte from the chromatography effluent flow stream during step (b) by applying an electrical potential across the stationary phase such that hydronium ions are generated at the anode and are flowed from the anode towards the cathode thereby driving electrolyte from the chromatography effluent flow stream and towards the cathode;
   (d) combining the analyte ions in the chromatography effluent flow stream with the hydronium ions during step (c); and
   (e) detecting the anions after step (d).

23. The method of claim 22 wherein the anions are detected while in the suppressor stationary phase.

24. The method of claim 22 wherein the anions are flowed from the suppressor stationary phase to a detector after step (d).

25. The method of claim 21 wherein the electrolyte is substantially precluded from entering the detector.

26. The method of claim 22 wherein the electrolyte is substantially removed from the chromatography effluent flow stream.

27. The method of claim 24 wherein oxygen gas is generated at the anode during step (c) and is removed from the chromatography effluent flow stream before the anions are detected.

28. The method of claim 22 wherein the suppressor stationary phase comprises a first stationary phase and a second stationary phase, the first stationary phase being substantially adjacent the anode and wherein the chromatography effluent stream is flowed through the first stationary phase.

29. The method of claim 28 wherein the first stationary phase remains substantially in its unexhausted form during. step (c).

30. The method of claim 28 wherein the electrolyte is substantially precluded from the first stationary phase.

31. A method of detecting cations by continuous electrochemical suppressed ion chromatography comprising
   (a) chromatographically separating cations in an aqueous mobile phase comprising electrolyte to form an aqueous chromatography effluent comprising separated cations and electrolyte;
   (b) flowing the aqueous chromatography effluent through a suppressor stationary phase that is in electrical communication with an anode and a cathode;
   (c) driving electrolyte from the chromatography effluent flow stream during step (b) by applying an electrical potential across the stationary phase, the application of the electrical potential generating hydroxide ions at the cathode, the hydroxide ions being flowed from the cathode towards the anode thereby driving the electrolyte from the chromatography effluent flow stream and towards the anode;
   (d) combining the cations in the chromatography effluent flow stream with the hydroxide ions during step (c); and
   (e) detecting the cations after step (d).

32. The method of claim 31 wherein the cations are detected while in the suppressor stationary phase.

33. The method of claim 31 wherein the cations are flowed from the suppressor stationary phase to a detector after step (d).

34. The method of claim 33 wherein the electrolyte is substantially precluded from entering the detector.

35. The method of claim 31 wherein the electrolyte is substantially removed from the chromatography effluent flow stream.

36. The method of claim 31 wherein hydrogen gas is generated at the cathode during step (c) and is removed from the chromatography effluent flow stream before the cations are detected.

37. The method of claim 31 wherein the suppressor stationary phase comprises a first stationary phase and a second stationary phase, the first stationary phase being substantially adjacent the cathode and wherein the chromatography effluent stream is flowed through the first stationary phase.

38. The method of claim 37 wherein the first stationary phase remains substantially in its unexhausted form during step (c).

39. The method of claim 37 wherein the electrolyte is substantially precluded from the first stationary phase.

* * * * *

UNITED STATES PATENT AND TRADEMARK OFFICE
CERTIFICATE OF CORRECTION

PATENT NO.    : 6,468,804 B1
DATED         : October 22, 2002
INVENTOR(S)   : J. M. Anderson, Jr. et al.

It is certified that error appears in the above-identified patent and that said Letters Patent is hereby corrected as shown below:

Column 14,
Line 33, delete "electrolytes" and substitute -- electrolyte is -- in its place.

Column 15,
Line 43, immediately after "form during" delete "." (period).

Signed and Sealed this

Sixth Day of May, 2003

JAMES E. ROGAN
*Director of the United States Patent and Trademark Office*